United States Patent
Levy

(10) Patent No.: US 11,844,777 B2
(45) Date of Patent: *Dec. 19, 2023

(54) METHODS OF TREATING AUTOIMMUNE MICROVASCULAR DISORDERS

(71) Applicant: PRIMUS PHARMACEUTICALS, INC., Scottsdale, AZ (US)

(72) Inventor: Robert M Levy, Fountain Hills, AZ (US)

(73) Assignee: Primus Pharmaceuticals, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/670,609

(22) Filed: Feb. 14, 2022

(65) Prior Publication Data

US 2022/0168267 A1 Jun. 2, 2022

Related U.S. Application Data

(63) Continuation of application No. 16/632,032, filed as application No. PCT/US2018/042573 on Jul. 18, 2018, now Pat. No. 11,278,517.

(60) Provisional application No. 62/534,237, filed on Jul. 19, 2017.

(51) Int. Cl.
| | |
|---|---|
| *A61K 31/352* | (2006.01) |
| *A61P 9/10* | (2006.01) |
| *A61K 9/14* | (2006.01) |
| *A61P 9/14* | (2006.01) |

(52) U.S. Cl.
CPC ............. *A61K 31/352* (2013.01); *A61P 9/10* (2018.01); *A61P 9/14* (2018.01)

(58) Field of Classification Search
CPC ............. A61K 31/352; A61P 9/10; A61P 9/14
See application file for complete search history.

(56) References Cited

U.S. PATENT DOCUMENTS

| | | | | |
|---|---|---|---|---|
| 6,147,054 A | * | 11/2000 | De Paoli Ambrosi | A61K 8/0216 |
| | | | | 424/732 |
| 2012/0208777 A1 | | 8/2012 | Wierzbicki et al. | |
| 2015/0164826 A1 | | 6/2015 | Cooper et al. | |

FOREIGN PATENT DOCUMENTS

WO 2015/153648 A1 10/2015

OTHER PUBLICATIONS

Misterska, et al., Systemic sclerodermia associated with chronic hepatits. Case report; Post Dermatol Alergol 2007; XXIV, 3: 144-149.
Nitsche, Alejandro; Raynaud, Digital Ulcers and Calcinosis in Scleroderma, Elsevier DOYMA; Reumatol Clin. 2012;8 (5):270-277.
Diosimin, Alternative Medicine Review; vol. 9, No. 3; 2004 5 pp.
International Application No. PCT/US2018/042573, filed Jul. 18, 2018, International Search Report and Written Opinion; ISA/US, dated Sep. 28, 2018, 10 pp.
Primus Pharmaceuticals, Inc.; EP Application No. 18836058.0; EP Supplemental Opinion dated Feb. 8, 2021; 2 pp.
Batchvarov, Ivan et al.; One-Year Diosimin Therapy (600 MG) in Patients With Chronic Venous Insufficiency—Results and Analysis; J. Biomed Clin Res vol. 3 No. 1, 2010; 4 pp.

\* cited by examiner

*Primary Examiner* — Timothy R Rozof
(74) *Attorney, Agent, or Firm* — Clark G. Sullivan

(57) ABSTRACT

Methods of treating autoimmune microvascular conditions using diosmin or diosmetin are described, particularly the treatment of digital ulcers in systemic sclerosis.

22 Claims, No Drawings

METHODS OF TREATING AUTOIMMUNE MICROVASCULAR DISORDERS

FIELD OF THE INVENTION

This invention relates to methods for treating autoimmune microvascular diseases and the complications thereof, including digital ulcers in scleroderma, using diosmin or diosmetin, or a pharmaceutically acceptable salt thereof.

BACKGROUND

Systemic sclerosis (a/k/a scleroderma) is a prototypical autoimmune microvascular disorder characterized by fibrosis and thickening of the skin and multi-organ involvement. The disease has a world-wide incidence rate of approximately 20 per million people per year and prevalence of approximately 240-280 per million (Mayes 2003a,b, Rosa 2011, Barnes 2012). Several forms and subsets are recognized. Diffuse systemic sclerosis affects skin and some combination of other organ systems. Limited systemic sclerosis affects skin, generally distal to the elbows and knees, and is associated with less internal organ involvement than diffuse systemic sclerosis. Morphea is a very limited form of cutaneous systemic sclerosis that produces localized patches of thickened, fibrotic skin but usually is not associated with internal organ involvement. The CREST syndrome (calcinosis, Raynaud's phenomenon, esophageal involvement, sclerodactyly, telangiectasias) is generally considered a subset of diffuse systemic sclerosis but may also be seen in limited systemic sclerosis (Hachula 2011).

Digital ischemia is a characteristic of systemic sclerosis being seen in more than 95% of patients (McMahan 2010). Digital ulcers contribute significantly to the morbidity, interference with life activities and cost of systemic sclerosis (Hughes 2016). An observational study using data from the RUSTAR database found that the most common subtype was limited cutaneous disease; 59% of patients had >2 ulcers, 67% had at least one hospital admission and 57% reported significant impairment of daily activities compared with 37% of patients without ulcers (Brand 2015).

Calcium channel blockers and vasodilators are considered first line treatment for systemic sclerosis. Bosentan, a drug primarily used for the treatment of pulmonary hypertension, was approved in the European Union in 2007 for reducing the number of new digital ulcers in patients with systemic sclerosis and ongoing digital ulcer disease. Iloprost is another drug used to treat pulmonary arterial hypertension (PAH), systemic sclerosis, Raynaud's phenomenon and other diseases in which the blood vessels are constricted and blood can't flow to the tissues. Response rates for all of these interventions is low.

Factors contributing to the development of digital ulcers include tight, thin skin, repeated microtrauma, calcinosis, underlying microvasculitis and chronic digital ischemia due to repeated episodes of Raynaud's phenomenon (Nitsche 2012, Hughes 2016). Capillary loss with avascular areas seen on capillaroscopy especially in the presence of elevated serum IL-6 levels are predictive of future ulcer development (Alivernini 2009, Lambova 2011, Cutolo 2013). Digital ulcers are extremely painful and slow to heal—as many as 32% will become chronic (Steen 2009, Doveri 2011)—and are associated with significant functional loss (Steen 1997, Khindas 2011, Berezne 2011). Ulcers located at the digital terminal tufts or extensor surfaces are thought to be due to ischemia from a combination of microvascular disease and actual capillary loss coupled with ischemia from vasospasm associated with Raynaud's phenomenon. Ulcers located over bony prominences are more likely due to repeated microtrauma and tissue ischemia from tightened, fibrotic skin superimposed on the underlying microvascular disease.

Microvascular disease is reportedly associated with the development of many of the clinical features of systemic sclerosis (Guiducci 2007). Capillary changes in systemic sclerosis are characteristic and worsen with disease progression (Camargo 2015). A capillaroscopic skin ulcer risk index (CSURI) has been developed which has sufficient predictive value of the potential for future ulcer development to be useful in designing aggressive preventive therapeutic regimens (Sebastiani 2009, Smith 2013). People who present with Raynaud's without other features of a systemic rheumatic disease and have abnormal capillaroscopic findings and one or more of the typical systemic sclerosis autoantibodies have a 60-fold greater chance of developing systemic sclerosis than Raynaud's patients without those findings (McMahon 2010).

Diosmin is a flavonoid present in low concentrations in citrus. When used commercially it is produced by simple oxidation of the closely related hesperidin, also extracted from citrus but present in much higher quantities than diosmin. Diosmetin is the aglycone of diosmin and the form found in blood after oral ingestion of diosmin (Cova 1992).

Diosmin has been used and approved in much of Europe and marketed under a variety of brand names, principally Daflon™, as a drug for treatment of chronic venous insufficiency and its complications, including venous ulcers and hemorrhoids, for more than three decades. In literature that runs to hundreds of papers, the vast majority has dealt with the molecular, phlebotonic and clinical effects of diosmin on the venous system which has been the primary historical therapeutic target for diosmin.

Attempts have been made to define and quantify the effects of diosmin on the microvasculature. Intravital microscopy was used to study the effects of diosmin in the streptozotocin-induced diabetic hamster cheek pouch model (Bouskela 1995). Pretreatment with diosmin significantly reduced the number of capillary leaks induced by each of the test articles, bradykinin, and LTB4. After reperfusion following 30 minutes of ischemia macromolecular permeability deceased as did the number of leukocytes adhering to the endothelium.

Diosmin has also been shown to inhibit the overexpression of leukocyte and endothelial cell adhesion molecules typically encountered in a variety of ischemia/reperfusion models (Shields 2004, Coleridge Smith 2000b). In another study (Bouskela 1997) using intravital microscopy following ischemia/reperfusion in the hamster cheek pouch model, untreated control animals showed significant arteriolar vasodilation, reduction in flow velocity and decrease in functional capillary density. Pretreatment with diosmin in doses of 2, 20, 80 and 160 mg/kg/d reversed all these changes towards normal in a dose dependent manner. In a related animal model (di Souza 2014), venous sclerosis was induced in rabbit ear veins by injection of 5% ethanolamine oleate. Treatment with diosmin 300 mg/kg/d beginning 7 days before sclerotherapy and continued for 4 days after the procedure prevented the increase in venous and arteriolar diameter, reduced the number of adherent leukocytes, reduced the number of capillary leakage sites, preserved functional capillary density and reduced perivenous edema ($p<0.001$ for all parameters).

In view of this background, it is an object of the present invention to develop an effective treatment for microvascular diseases, particularly autoimmune microvascular diseases, and especially systemic sclerosis, including but not limited to ulcers and digital ulcers in subjects with systemic sclerosis.

It is another object to provide new uses for diosmin and diosmetin and pharmaceutically acceptable salts thereof.

SUMMARY OF THE INVENTION

The inventors have unexpectedly discovered that diosmin has the ability to treat the microvasculitis that is associated with systemic sclerosis, and the digital ulcers that occur in patients with systemic sclerosis. Based on these discoveries, the inventors have in a first principal embodiment developed a method of treating an autoimmune microvascular disease in a subject in need thereof, comprising administering to said subject a therapeutically effective amount of diosmin or diosmetin, or a pharmaceutically acceptable salt thereof, for a therapeutically effective period of time.

In a second principal embodiment, the inventors have developed a method of treating an ulcer in a subject with an autoimmune microvascular disease comprising administering to said subject a therapeutically effective amount of diosmin or diosmetin, or a pharmaceutically acceptable salt thereof, for a therapeutically effective period of time.

In a third principal embodiment, the inventors have developed a method of treating an ulcer in a subject with systemic sclerosis comprising administering to said subject a therapeutically effective amount of diosmin or diosmetin, or a pharmaceutically acceptable salt thereof, for a therapeutically effective period of time.

In a fourth principal embodiment, the inventors have developed a method of treating a digital ulcer in a subject with systemic sclerosis comprising administering to said subject a therapeutically effective amount of diosmin or diosmetin, or a pharmaceutically acceptable salt thereof, for a therapeutically effective period of time. Additional aspects and advantages of the invention are set forth in part in the description that follows, and in part will be obvious from the description, or may be learned by practice of the invention. The aspects and advantages will be realized and attained by means of the elements and combinations particularly pointed out in the detailed description and appended claims. It is to be understood that both the foregoing general description and the following detailed description are exemplary and explanatory only and are not restrictive of the invention, as claimed.

DETAILED DESCRIPTION

Definition and Use of Terms

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

When the singular forms "a," "an" and "the" or like terms are used herein, they will be understood to include plural referents unless the context clearly dictates otherwise. Thus, for example, reference to "an excipient" includes mixtures of two or more such excipients, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality of components, steps or conditions, it will be understood that the element can also be described as comprising any combination of such plurality, or "consisting of" or "consisting essentially of" the plurality or combination of components, steps or conditions.

"Diosmin" is a naturally occurring flavonoid glycoside that can be isolated from various plant sources or derived from the flavonoid hesperidin. The molecule has the following chemical structure:

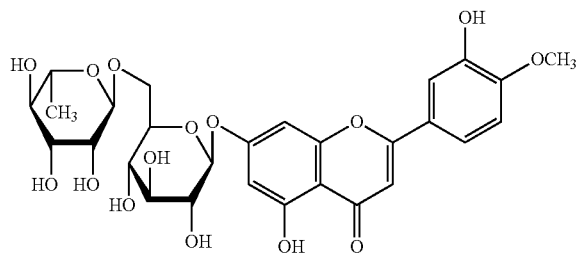

Diosmin is chemically described as (7-[[6-O-(6-Deoxy-α-L-mannopyranosyl)-β-D-glucopyranosyl]oxy]-5-hydroxy-2-(3-hydroxy-4-methoxyphenyl)-4H-1-benzopyran-4-one) with a molecular weight of 608.5.

The molecule is commonly supplied in what is referred to as a micronized purified flavonoid fraction ("MPFF"), which includes various related compounds in concentrations commonly up to 10%. For purposes of this invention, diosmin refers to the actual diosmin content in the relevant dosage form or method, excluding these related compounds.

Diosmetin is the aglycone/active metabolite of diosmin to which diosmin is converted following oral administration and other routes of delivery. Diosmetin has the following chemical structure:

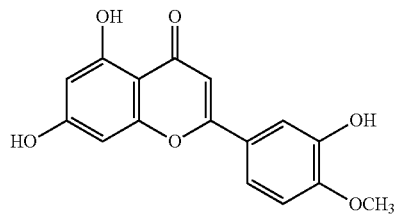 [SMILES: COc1ccc(-c2cc(=O)c3c(O)cc(O)cc3o2)cc1O]

The compound is known chemically as 5,7-Dihydroxy-2-(3-hydroxy-4-methoxyphenyl)-4H-1-benzopyran-4-one, with a molecular weight of 300.266 g/mol.

When ranges are given by specifying the lower end of a range separately from the upper end of the range, or specifying particular numerical values, it will be understood that a separate range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for human or veterinary pharmaceutical use. "Pharmaceutically acceptable salts" means salts that are pharmaceutically acceptable, as defined above, and which possess the desired pharmacological activity.

When a dose of a drug or its pharmaceutically acceptable salt is described herein, it will be understood that the dose is based on the weight of the free base, excluding any hydrates or solvates thereof, unless the description states that the dose is based on the weight of the salt, hydrate or solvate.

"Digital ulcer" as used in this application refers to an open sore on an external surface of the body, most commonly on the fingers or toes, caused by a break in the skin that fails to heal.

A "microvessel" refers to a blood vessel of the microvasculature, preferably having a mean diameter of less than 100 or 70 micrometers. In like manner, a "microvascular disease" refers to a disease that predominantly and preferably affects microvasculature less than about 100 or 70 micrometers in diameter.

An "autoimmune microvascular disease" refers to a disease affecting the integrity of the body's microvessels occurring in the presence of a systemic immunologic disorder.

Principal Embodiments

The invention is described herein in terms of principal embodiments and subembodiments. It will be understood that each of the subembodiments can modify any of the principal embodiments, unless such modification is logically inconsistent or expressly disallowed in this document. It will be further understood that the principal embodiments can be combined in any manner, and that the subembodiments can be combined in any manner to further modify any of the principal embodiments, unless such combination is logically inconsistent or expressly disallowed in this document.

In a first principal embodiment, the invention provides a method of treating an autoimmune microvascular disease in a subject in need thereof, comprising administering to said subject a therapeutically effective amount of diosmin or diosmetin, or a pharmaceutically acceptable salt thereof, for a therapeutically effective period of time.

In a second principal embodiment, the invention provides a method of treating an ulcer in a subject with an autoimmune microvascular disease comprising administering to said subject a therapeutically effective amount of diosmin or diosmetin, or a pharmaceutically acceptable salt thereof, for a therapeutically effective period of time.

In a third principal embodiment, the invention provides a method of treating an ulcer in a subject with systemic sclerosis, comprising administering to said subject a therapeutically effective amount of diosmin or diosmetin, or a pharmaceutically acceptable salt thereof, for a therapeutically effective period of time.

In a fourth principal embodiment, the invention provides a method of treating a digital ulcer in a subject with systemic sclerosis, comprising administering to said subject a therapeutically effective amount of diosmin or diosmetin, or a pharmaceutically acceptable salt thereof, for a therapeutically effective period of time.

Subembodiments

The invention can further be defined in terms of various subembodiments. In one subembodiment, the methods of the present invention are for treating an ulcer in a subject with an autoimmune microvascular disease. In another subembodiment, the methods of the present invention are for treating an ulcer in a subject with systemic sclerosis. In still another subembodiment, the methods of the present invention are for treating a digital ulcer in a subject with systemic sclerosis.

In one subembodiment the subject has microvasculitis. In another subembodiment the subject has microvasculitis in terminal arterial vessels or capillaries. In still another subembodiment the subject has non-venous microvasculitis. In yet another subembodiment the subject has non-venous microvasculitis in terminal arterial vessels or capillaries.

In one particular subembodiment the methods of the present invention are used to treat an autoimmune microvascular disease, and the disease is selected from rheumatoid arthritis, systemic lupus erythematosus, Sjögren syndrome, systemic sclerosis, dermatomyositis, mixed connective tissue disease, leukoclastic vasculitis, antiphospholipid antibody syndrome, and paraproteinemias including cryoglobulinemia and cryofibrinogenemia.

The method also can be defined based on a clinical characterization of the affected patient. Thus, in one subembodiment, the subject has a sclerotic condition selected from diffuse systemic sclerosis, limited systemic sclerosis, and morphea. In another subembodiment the subject has CREST syndrome. In another subembodiment the subject has one or more digital ulcers resulting from digital ischemia and Raynaud's disease. In still another subembodiment the subject has one or more digital ulcers due to ischemia from a combination of microvascular disease and actual capillary loss coupled with ischemia from vasospasm associated with Raynaud's disease.

The dose employed will depend on the nature and severity of the disease, the route of administration, and other factors known to workers of ordinary skill in the art. In one particular embodiment, the therapeutically effective amount is from 300 to 5000 mg for diosmin, or from 150 to 2500 mg for diosmetin, or a pharmaceutically acceptable salt thereof, administered orally to the subject on a daily basis, preferably divided into two separate doses. In another particular embodiment, the therapeutically effective amount is from 400 to 2000 mg for diosmin, or from 200 to 1000 mg for diosmetin, or a pharmaceutically acceptable salt thereof, administered orally to the subject on a daily basis, preferably divided into two separate doses. In still another particular embodiment, the therapeutically effective amount is from 800 to 1200 mg for diosmin, or from 400 to 600 mg for diosmetin, or a pharmaceutically acceptable salt thereof, administered orally to the subject on a daily basis, preferably divided into two separate doses.

In any of the foregoing principal embodiments or subembodiments, the diosmin or diosmetin is administered to the subject for at least 4 weeks, 8 weeks, 12 weeks, 3 months or 6 months. I.e., the therapeutically effective period of time is at least 4 weeks, 8 weeks, 12 weeks, 3 months or 6 months.

In any of the foregoing principal embodiments or subembodiments, the subject is an adult having an age of 18 years or older.

In any of the foregoing embodiments, the method is preferably carried out in conjunction with one or more of the following treatment methods:

Prevention of cold exposure
Removal of necrotic or infected tissue
Management of wound infection
Wound cleansing
Nutritional support
Support bandaging In general, clinical outcomes associated with the use of the treatment of the present invention can be broadly grouped into two categories: improved wound healing and improved wound care.

Complete wound closure of a chronic, non-healing ulcer is one of the most objective and clinically meaningful wound healing endpoints. Complete wound closure is defined as skin re-epithelialization without drainage or dressing requirements, preferably confirmed in the clinical setting at two consecutive study visits 2 weeks apart.

The efficacy of the treatment also can be evaluated based on accelerated wound closure. This, in another subembodiment the treatment provides a clinically meaningful reduction in the time to healing using a time-to-event analysis (the event being complete closure).

In a preferred subembodiment, the invention is used for the treatment of ulcers or digital ulcers, and the treatment has been shown to either completely heal the ulcer, or to reduce the size of the ulcer, relative to placebo.

Dosage Forms/Routes of Administration

Pharmaceutical compositions for preventing and/or treating a subject are further provided comprising a therapeutically effective amount of diosmin or diosmetin, or a pharmaceutically acceptable salt thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. In a preferred embodiment, the active compounds and compositions, are administered orally or topically.

Suitable carriers and their formulations are described in Remington: The Science and Practice of Pharmacy (19th ed.) ed. A. R. Gennaro, Mack Publishing Company, Easton, Pa., 1995. Oral administration of a solid dose form can be, for example, presented in discrete units, such as hard or soft capsules, pills, cachets, lozenges, or tablets, each containing a predetermined amount of at least one of the disclosed compound or compositions. In some forms, the oral administration can be in a powder or granule form. In some forms, the oral dose form is sub-lingual, such as, for example, a lozenge. In such solid dosage forms, the compounds of the present invention are ordinarily combined with one or more excipients. Such capsules or tablets can contain a controlled-release formulation. In the case of capsules, tablets, and pills, the dosage forms also can comprise buffering agents or can be prepared with enteric coatings.

In some forms, oral administration can be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. In other forms, the disclosed compositions can comprise a topical dose form. Other carrier materials and modes of administration known in the pharmaceutical art can also be used. The disclosed pharmaceutical compositions can be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients (3.sup.rd Ed.), American Pharmaceutical Association, Washington, 1999.

The disclosed compounds can be used, alone or in combination with other therapeutic agents, in the treatment or prevention of various conditions or disease states. The administration of two or more compounds "in combination" means that the two compounds are administered closely enough in time that the presence of one alters the biological effects of the other. The two or more compounds can be administered simultaneously, concurrently or sequentially.

EXAMPLES

In the following study, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Diosmin in the Treatment of Digital Ulcers

To evaluate the effect of diosmin on Raynaud's and digital ulcers, a randomized, double blind, placebo controlled clinical trial was conducted. In this trial, subjects were randomized to receive either 600 mg of diosmin or matching placebo twice daily. The trial recorded improvement/healing of ulcers. Subjects with ulcers who were not on active ulcer therapy were required to have at least one stable or worsening digital ulcer for at least one month and subjects receiving ulcer therapy were required to have at least one stable or worsening ulcer on stable therapy for at least two months and therapy was required to remain constant for the duration of the trial.

The results of this trial of ulcer patients are reported in Table 1.

TABLE 1

Ulcer Response Diagnosis All Digital Ulcers
(including 9 ulcers in 4 non-scleroderma subjects)

| Parameter | Visit | Active | Placebo | p-value* |
|---|---|---|---|---|
| Number of Ulcers at Baseline | Baseline | 43 | 13 | |
| Number of New Ulcers Appearing between Baseline and Week 4 | Week 4 | 14 | 1 | |
| Number (%) of Ulcers Healed at Week 4 Relative to Baseline | Week 4 | 18/43 (41.9%) | 2/13 (15.4%) | 0.1251 |
| Number (%) of Ulcers Healed at Week 8 Relative to Baseline | Week 8 | 31/42 (73.8%) | 3/13 (23.1%) | 0.0113 |
| Number (%) of Ulcers Healed at Week 8 Relative to Week 4 | Week 8 | 18/37 (48.6%) | 1/12 (8.3%) | 0.0600 |
| Number (%) with >= 50% Improvement at Week 4 Relative to Baseline | Week 4 | 23/43 (53.5%) | 3/13 (23.1%) | 0.0905 |
| Number (%) with >= 50% Improvement at Week 8 Relative to Baseline | Week 8 | 39/42 (92.9%) | 4/13 (30.8%) | 0.0018 |
| Number (%) with >= 50% Improvement at Week 8 Relative to Week 4 | Week 8 | 25/37 (67.6%) | 2/12 (16.7%) | 0.0207 |

*p-value generated assuming a binomial distribution and logit link with fixed effect of Treatment and Subject as the repeated term.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

CITED REFERENCES

1. DIOSMIN Monograph, Alternative Medicine Review, Volume 9, Number 3 (2004).
2. Alivernini S, De Santis M, Tolusso B, et al. Skin ulcers in systemic sclerosis: determinants of presence and predictive factors of healing. J Am Acad Dermatol. 2009.60: 426-35.
3. Berezne A, Seror R, Morell-Dubois, et al. Impact of systemic sclerosis on occupational and professional activity with attention to patients with digital ulcers. Arth Care Res. 2011.63:277-85.
4. Bouskela E, Donyo K A. Effects of oral administration of purified flavonoid fraction on increased microvascular permeability induced by various agents and on ischemia/ reperfusion in diabetic hamsters. Int J Microcirc Clin Exp. 1995.15:293-300.
5. Bouskela E, Cyrino F Z, Lerond L. Effects of oral administration of different doses of purified micronized flavonoid fraction on microvascular reactivity after ischemia/reperfusion in the hamster cheek pouch. Br J Pharmacol. 1997.122:1611-6.
6. Brand M, Hollaender R, Rosenberg D, et al. An observational cohort study of patients with newly diagnosed digital ulcer disease secondary to systemic sclerosis registered in the EUSTAR database. Clin Exp Rheumatol. 2015.33 (suppl 91): 547-54.
7. Camargo C Z, Sekiyama J Y, Arismendi M I, Kayser C. Microvascular abnormalities in patients with early systemic sclerosis; less severe morphological changes than in patients with definite disease. Scand J Rheumatol. 2015.44:48-55.
8. Coleridge Smith P D. Micronized purified flavonoid fraction and the treatment of chronic venous insufficiency: microcirculatory mechanisms. Microcirculation. 2000b.7: S35-40.
9. Cutolo M, Pizzotni C, Secci M E, Sulli A. Capillaroscopy. Best Prac Re Clin Rheumatol. 2008.22:1093-108.
10. Cyrino F Z, Bottino D A, Lerond L, Bouskela E. Micronization enhances the protective effect of purified flavonoid fraction against postischemic microvascular injury in the hamster cheek pouch. Clin Exp Pharmacol Physiol. 2004.31:159-62.
11. De Souza M D, Cyrino F Z, Mayall M R, et al. Beneficial effects of the micronized purified flavonoid fraction (MPFF), Daflon® 500 mg) on microvascular damage elicited by sclerotherapy. Phlebology 2016.31:50-6.
12. Doveri M, Della Rossa A, Salcadori S, et al. Systemic sclerosis: outcome and long term follow-up of 429 patients from a single Italian centre. Ann Rheum Dis. 2011.70(suppl 3):660.
13. Hachulla E, Launay D. Diagnosis and classification of systemic sclerosis. Clin Rev Allergy Immunol. 2011.40: 78-83.
14. Hamaguchi Y. Autoantibody profiles in systemic sclerosis: predictive value for clinical evaluation and prognosis, J Dermatol. 2010.37:42-53.
15. Hanke K, Bruckner C S, Dahnrich C, et al. Antibodies against PM/Scl-75 and PM/Scl-100 are independent markers for different subsets of systemic sclerosis patients, Arth Res Ther. 2009.11: R22. Doi. 10.1186/ar2614
16. Hughes M, Herrick A L. Digital ulcers in systemic sclerosis. Rheumatology. 2016.doi:10.1093/rheumatology/kew047. Epub ahead of print.
17. Khimdas S, Harding S, Bonner A, et al. Associations with digital ulcers in a large cohort of systemic sclerosis:

results from the Canadian Scleroderma Research Group Registry. Arth Care Res. 2011.63:142-9.
18. Mayes M D. Scleroderma epidemiology. Rheu Clin N A. 2003a.29:239-54.
19. Mayes M D, Lacey J V Jr, Beebe-Dimmer J, et al. Prevalence, incidence, survival and disease characteristics of systemic sclerosis in a large US population. Arth Rheu.2003b.48:2246-55.
20. McMahan Z H, Wigley F M. Raynaud's phenomenon and digital ulcers: a practical approach to risk stratification, diagnosis and management. Int J Clin Rheumatol. 2020.5:355-70.
21. Nitsche A. Raynaud, digital ulcers and calcinosis in scleroderma. Rheumatologia Clinica. 2012.8. 270-7.
22. Ruaro B, Smith V, Sulli A, et al. Methods for the morphological and functional evaluation of microvasculature damage in systemic sclerosis, Korean J Int Med. 2015.30:1-5.
23. Sebastiani M, Manfredi A, Colaci M, et al., Capillaroscopic skin ulcer risk index: a new prognostic tool for digital skin ulcer development in systemic sclerosis patients, Arth Rheum 2009.61:688-94.
24. Shields D A. Andaz S K. Abeysinghe R D, et al. Neutrophil activation in experimental ambulatory venous hypertension. Phlebology. 1994.9" 119-24.
25. Steen V D, Medsger T A. The value of the Health Assessment Questionnaire and special patients generate scales to demonstrate change in systemic sclerosis patients over time. Arth Rheum 1997.40:1984-91.
26. Steen V, Denton C P, Pope J, Matucci-Cerinic M. Digital ulcers: overt vascular disease in systemic sclerosis. Rheumatol. 2009.4(suppl 3):19-24.
27. Sulli A, Secchi M E, Pizzorni C, Cutolo M. Scoring the nailfold microvascular changes during the capillaroscopic analysis in systemic sclerosis. Ann Rheu Dis. 2008.67: 885-7.
28. Tavakot M E, Fatemi A, Karbalalaie A, et al. Nailfold capillaroscopy in rheumatic diseases: which parameters should be evaluated. Biomed Res Int. 2015. Sep. 1 doi:10.1155/2015/974530.
29. Vanthuyne M, Smith V, De Langhe E, et al. The Belgian systemic sclerosis cohort: correlations between disease severity scores, cutaneous subsets, and antibody profile. J Rheumatol. 2012.39:2127-33.
30. Cova D, De Anfelia L, Giavarini F, et al. Pharmacokinetics and metabolism of oral diosmin in healthy volunteers. Int J Clin Pharmacol, Ther Toxicol. 1992.30:29-33.
31. Cutolo, M, Pizzorni C, Sulli A, Smith V. Early diagnostic and predictive value of capillaroscopy in systemic sclerosis. Curr Rheumatol Rev. 2013.9:249-53.
32. Lambova S, Miller-Ladner U. Capillaroscopic findings in systemic sclerosis—are they associated with disease duration and presence of digital ulcers? Discov Med. 2011.66:413-8.
33. Pavlov-Dolijanovic S, Damajanov N, Ostojoc P, et sl. The prognostic value of nailfold capillary changes for the development of connective tissue disease in children and adolescents with primary Raynaud phenomenon: a follow-up study of 250 patients. Pediatr Dermatol. 2006.23: 437-42.
34. Smith V R, Pizzorni C, Decuman S, et al. Nailfold capillaroscopy for prediction of novel future severe organ involvement in systemic sclerosis. J Rheumatol. 2013.40: 2023-8.

The invention claimed is:

1. A method of treating an autoimmune microvascular disease in a subject in need thereof, comprising orally administering to said subject a formulation comprising as the sole active ingredient a therapeutically effective amount of diosmin or diosmetin, or a pharmaceutically acceptable salt thereof, or a combination thereof, for a therapeutically effective period of time.

2. A method of treating an ulcer in a subject with an autoimmune microvascular disease comprising orally administering to said subject a formulation comprising as the sole active ingredient a therapeutically effective amount of diosmin or diosmetin, or a pharmaceutically acceptable salt thereof, or a combination thereof, for a therapeutically effective period of time.

3. A method of treating an ulcer in a subject with systemic sclerosis comprising orally administering to said subject a formulation comprising as the sole active ingredient a therapeutically effective amount of diosmin or diosmetin, or a pharmaceutically acceptable salt thereof, or a combination thereof, for a therapeutically effective period of time.

4. A method of treating a digital ulcer in a subject with systemic sclerosis, comprising orally administering to said subject a formulation comprising as the sole active ingredient a therapeutically effective amount of diosmin or diosmetin, or a pharmaceutically acceptable salt thereof, or a combination thereof, for a therapeutically effective period of time.

5. The method of claim 1 for treating an ulcer in a subject with an autoimmune microvascular disease.

6. The method of claim 1 for treating an ulcer in a subject with systemic sclerosis.

7. The method of claim 1 wherein said autoimmune vascular disease is selected from rheumatoid arthritis, systemic lupus erythematosus, Sjögren disease, systemic sclerosis, dermatomyositis, mixed connective tissue disease, leukoclastic vasculitis, antiphospholipid antibody syndrome, and paraproteinemias including cryoglobulinemia and cryofibrinogenemia.

8. The method of claim 1, for treating a digital ulcer in a patient with systemic sclerosis.

9. The method of claim 1, wherein the subject has microvasculitis.

10. The method of claim 1, wherein the subject has microvasculitis in terminal arterial vessels or capillaries.

11. The method of claim 1, wherein the subject has non-venous microvasculitis.

12. The method of claim 1, wherein the subject has non-venous microvasculitis in terminal arterial vessels or capillaries.

13. The method of claim 1, wherein said subject has a sclerotic condition selected from diffuse systemic sclerosis, limited systemic sclerosis, and morphea.

14. The method of claim 1, wherein said subject has CREST syndrome.

15. The method of claim 1, wherein said subject has one or more digital ulcers resulting from digital ischemia and secondary Raynaud's phenomenon.

16. The method of claim 1, wherein said subject has one or more digital ulcers due to ischemia from a combination of microvascular disease and actual capillary loss coupled with ischemia from vasospasm associated with secondary Raynaud's phenomenon.

17. The method of claim 1, wherein said therapeutically effective amount is from 300 to 5000 mg of diosmin or a pharmaceutically acceptable salt thereof, administered orally to the subject on a daily basis.

18. The method of claim 1, wherein said therapeutically effective amount is from 150 to 2500 mg of diosmetin, or a pharmaceutically acceptable salt thereof, administered orally to the subject on a daily basis.

19. The method of claim 1, wherein said therapeutically effective amount is from 400 to 2000 mg of diosmin, or a pharmaceutically acceptable salt thereof, administered orally to the subject on a daily basis.

20. The method of claim 1, wherein said therapeutically effective amount is from 200 to 1000 mg of diosmetin, or a pharmaceutically acceptable salt thereof, administered orally to the subject.

21. The method of claim 1, wherein said therapeutically effective amount is from 800 to 1200 mg of diosmin or a pharmaceutically acceptable salt thereof, administered orally to the subject on a daily basis.

22. The method of claim 1, wherein said therapeutically effective amount is from 400 to 600 mg of diosmetin, or a pharmaceutically acceptable salt thereof, administered orally to the subject on a daily basis.

* * * * *